United States Patent
Adams et al.

(10) Patent No.: US 9,611,321 B2
(45) Date of Patent: Apr. 4, 2017

(54) RATIONALLY-DESIGNED ANTI-MULLERIAN INHIBITING SUBSTANCE TYPE II RECEPTOR ANTIBODIES

(75) Inventors: Gregory P. Adams, Hatboro, PA (US); Heidi H. Simmons, Willow Grove, PA (US); Matthew K. Robinson, Blue Bell, PA (US); Roland Dunbrack, Philadelphia, PA (US); Andreas Lehmann, Bear, DE (US)

(73) Assignee: Fox Chase Cancer Center, Philadelphia, PA (US)

( * ) Notice: Subject to any disclaimer, the term of this patent is extended or adjusted under 35 U.S.C. 154(b) by 176 days.

(21) Appl. No.: 14/122,286

(22) PCT Filed: May 29, 2012

(86) PCT No.: PCT/US2012/039831
§ 371 (c)(1),
(2), (4) Date: Apr. 29, 2014

(87) PCT Pub. No.: WO2012/166712
PCT Pub. Date: Dec. 6, 2012

(65) Prior Publication Data
US 2014/0234213 A1    Aug. 21, 2014

Related U.S. Application Data

(60) Provisional application No. 61/490,852, filed on May 27, 2011.

(51) Int. Cl.
| | | |
|---|---|---|
| *C07K 16/28* | (2006.01) | |
| *C07K 16/44* | (2006.01) | |
| *C07K 16/46* | (2006.01) | |
| *A61K 39/395* | (2006.01) | |
| *A61K 45/06* | (2006.01) | |

(52) U.S. Cl.
CPC .......... *C07K 16/28* (2013.01); *A61K 39/3955* (2013.01); *A61K 45/06* (2013.01); *C07K 16/44* (2013.01); *C07K 2317/565* (2013.01); *C07K 2317/622* (2013.01); *C07K 2318/10* (2013.01)

(58) Field of Classification Search
CPC .. C07K 16/28; C07K 16/46; C07K 2317/565; C07K 2317/622; C07K 2318/10; A61K 39/3955; A61K 45/06
See application file for complete search history.

(56) References Cited

U.S. PATENT DOCUMENTS

| | | |
|---|---|---|
| 2006/0099202 A1 | 5/2006 | Nicolette et al. |
| 2006/0188440 A1 | 8/2006 | Adams et al. |
| 2006/0216294 A1 | 9/2006 | McLennan et al. |
| 2010/0135996 A1 | 6/2010 | Teulon et al. |

FOREIGN PATENT DOCUMENTS

WO    WO 99/25379    5/1999

OTHER PUBLICATIONS

Frederickson, S., et al., "A Rationally Designed Agonist Antibody Fragment that Functionally Mimics Thrombopoietin," PNAS (2006) 103(39):14307-14312.
Simon, P.J., et al., "Display of Somatostatin-related Peptides in the Complementarity Determining regions of an Antibody Light Chain," Archives of Biochemistry and Biophysics (2005) 440:148-157.
Sollazzo, M., et al., "Expression of an Exogenous Peptide Epitope Genetically Engineered in the Variable Domain of an Immunoglobulin: Implications for Antibody and Peptide Folding," Protein Engineering (1990) 4(2):215-220.
Lefevre, G., et al., "Anti-idiotypic Antibodies to a Monoclonal Antibody Raised Against Anti-Mullerian Hormone Exhibit Anti-Mullerian Biological Activity," Molecular and Cellular Endocrinology (1989) 62:125-133.
Cate, R.L., et al., "Isolation of the Bovine and Human Genes for Mullerian Inhibiting Substance and Expression of the Human Gene in Animal Cells," Cell (1986) 45:685-698.
Salhi, I., et al. "The anti-Müllerian hormone type II receptor: insights into the binding domains recognized by a monoclonal antibody and the natural ligand." Biochem J. May 1, 2004;379(Pt 3):785-93.

*Primary Examiner* — Ruixiang Li
(74) *Attorney, Agent, or Firm* — Robert C. Netter, Jr.; Dann, Dorfman, Herrell and Skillman

(57) ABSTRACT

Methods for generating hybrid antibodies are provided.

14 Claims, 14 Drawing Sheets

Figure 1:
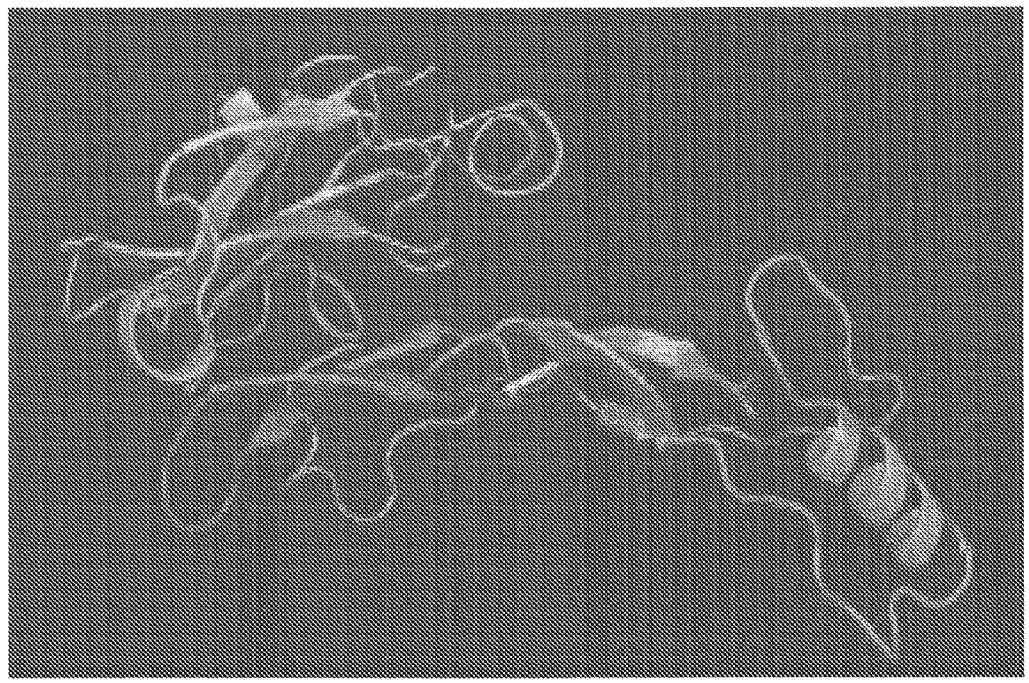

```
atggcccaggtacagctgcagcagtcaggtccaggactgg  40
tgaagccctcgcagaccctctcactcacctgtgccatctc  80
cggggacagtgtctctagcaagagtgctacttggaactgg  120
atcaggcagtccccatcgagaggccttgagtggctgggaa  160
ggacatacaggtccaagtggtataatgattatgcaga    200
gtctgtgaaagtcgataaccatcaagccagacacaacc   240
aagaaccattctccctgcagctgaagtctgtgactccg   280
aggacacggctgtgtattactgtGCAAGTGGAAATGGATA 320
TCTGGCCTACtggggccagggcacctggtcaccgtctcc    360
tcatcggcctcggggggccgaattgggcggcggcggctccg 400
gaggaggaggatctggtggtggtggttcgactagtcaggc  440
tgtgctgactcagccgtcctcagcgtctgggacccccggg  480
cagagggtcaccatctcttgttctggaagcagctccaaca  520
tcggggcaggctatgatgtacactggtaccagcagcttcc  560
aggaacagcccccaaactcctcatctatggtaacagcaat  600
cggccctcagggtccctgaccgattctctggctccaagt   640
ctggcacctcagcctcctggccatcactgggctccaggc   680
tgaggatgaggctgattattactgccagtccTATGACAGC 720
AGCCTGAGTGCCATAATTATGTCttcggaactgggacca    760
aggtcaccctcctaggctcgagccatcaccatcatcacca  800
ttaa                                      804
```

Figure 5A

```
atggcccaggtacagctgcagcagtcaggtccaggactgg   40
tgaagccctcgcagaccctctcactcacctgtgccatctc   80
cggggacagtgtctctagcaagagtgctacttggaactgg  120
atcaggcagtccccatcgagaggccttgagtggctgggaa  160
ggacatacaggtccaagtggtataatgattatgcaga     200
gtctgtgaaagtcgaataaccatcaagccagacacaacc   240
aagaaccattctcctgcagctgaagtctgtgactccg     280
aggacacgctgtgtattactgtGCAAGTGGAAATGGATA   320
TCTGGCCTACtggggccagggcacctggtcaccgtctcc   360
tcatcggcctcggggccgaattgggcggcggcggctccg   400
gaggaggaggatctggtggtggtggttcgactagtcaggc  440
tgtgctgactcagccgtcctcagcgtctgggaccccggg   480
cagagggtcaccatctcttgttctggaagcagctccaaca  520
tcggggcaggctatgatgtacactggtaccagcagcttcc  560
aggaacagcccccaaactcctcatctatggtaacagcaat  600
cggccctcaggggtccctgaccgattctctggctccaagt  640
ctggcacctcagcctccctggccatcactgggctccaggc  680
tgaggatgaggctgattattgccagtccTATGACAGC     720
AGCCTGAGTGCCCATAATTATGTCttcggaactgggacca  760
aggtcaccctcctaggc                         777
```

Figure 5B

```
atggcccaggtacagctgcagcagtcaggtccaggactgg   40
tgaagccctcgcagaccctctcactcacctgtgccatctc   80
cggggacagtgtctctagcaagagtgctacttggaactgg  120
atcaggcagtccccatcgagaggccttgagtggctgggaa  160
ggacatacaggtccaagtggtataatgattatgcaga     200
gtctgtgaaagtcgataaccatcaagccagacacaacc    240
agaaccattctccctgcagctgaagtctgtgactcccg    280
aggacacggctgtgtattactgtACCACCGACGGCTTCAT  320
CGGCAAGCTGCTCATCAGCCTGTCGGAGGAACGCATCAGC  360
GCGCACCACGTCCCTACTACTACATGGACGTCtggggcc   400
agggcacctggtcaccgtctcctcatcggcctcggggc    440
cgaattgggcggcggcggctccggaggaggaggatctggt  480
ggtggtggttcgactagtcaggctgtgctgactcagccgt  520
cctcagcgtctgggaccccgggcagaggtcaccatctc    560
ttgttctggaagcagctccaacatcggggcaggctatgat  600
gtacactggtaccagcagcttccaggaacagcccccaaac  640
tcctcatctatggtaacagcaatcggccctcaggggtccc  680
tgaccgattctctggctccaagtctggcacctcagcctcc  720
ctggccatcactgggctccaggctgaggatgaggctgatt  760
attactgccagtcctatgacagcagcctgagtgccataa   800
ttatgtcttcggaactgggaccaaggtcaccctcctaggc  840
```

```
atggcccaggtacagctgcagcagtcaggtccaggactgg  40
tgaagccctcgcagaccctctcactcacctgtgccatctc  80
cggggacagtgtctctagcaagagtgctacttggaactgg  120
atcaggcagtccccatcgagaggccttgagtggctgggaa  160
ggacatacaggtccaagtggtataatgattatgcaga    200
gtctgtgaaagtcgataaccatcaagccagacacaacc    240
aagaaccattctccctgcagctgaagtctgtgactcccg   280
aggacacggctgtgtattactgcaagtggaaatggata    320
tctggcctactggggccagggcacctggtcaccgtctcc   360
tcatcggcctcggggccgaattgggcggcggcggctccg   400
gaggaggaggatctggtggtggtggttcgactagtcaggc  440
tgtgctgactcagccgtcctcagcgtctgggaccccggg   480
cagagggtcaccatctcttgttctggaagcagctccaaca  520
tcggggcaggctatgatgtacactggtaccagcagcttcc  560
aggaacagcccccaaactcctcatctatggtaacagcaat  600
cggccctcaggggtccctgaccgattctctggctccaagt  640
ctggcacctcagcctccctggccatcactgggctccaggc  680
tgaggatgaggctgattattactgccagtccGGCAAGCTG  720
CTCATCAGCCTGTCGGAGGAACGCATCAGCGCGCACCACG  760
TCCCCCGCttcggaactgggaccaaggtcaccctctagg    800
c                                         801
```

```
atggcccaggtacagctgcagcagtcaggtccaggactgg  40
tgaagccctcgcagaccctctcactcacctgtgccatctc  80
cggggacagtgtctagcaagagtgctacttggaactgg   120
atcaggcagtccccatcgagaggccttgagtggctgggaa 160
ggacatacaggtccaagtggtataatgattatgcaga    200
gtctgtgaaagtcgataaccatcaagccagacacaacc   240
aagaaccattctccctgcagctgaagtctgtgactcccg  280
aggacacggctgtgtattactgtGCGAGCCCCCCGGCGG  320
CAAGCTGCTCATCAGCCTGTCGGAGGAACGCATCAGCGCG 360
CACCACGTCCCCATGGACTACtggggcagggcaccctgg  400
tcaccgtctcctcatcggcctcggggccgaattgggcgg  440
cggcggctccggaggaggaggatctggtggtggtggttcg 480
actagtcaggctgtgctgactcagccgtcctcagcgtctg 520
gaccccgggcagagggtcaccatctcttgttctggaag   560
cagctccaacatcggggcaggctatgatgtacactggtac 600
cagcagcttccaggaacagcccccaaactcctcatctatg 640
gtaacagcaatcggccctcaggggtccctgaccgattctc 680
tggctccaagtctggcacctcagctccctggccatcact  720
gggctccaggctgaggatgaggctgattattactgccagt 760
cctatgacagcagcctgagtgcccataattatgtcttcgg 800
aactgggaccaaggtcaccctcctaggc             828
```

Figure 8A

```
MAQVQLQQSGPGLVKPSQTL    20
SLTCAISGDSVSSKSATWNW    40
IRQSPSRGLEWLGRTYYRSK    60
WYNDYAESVKSRITIKPDTT    80
KNHFSLQLKSVTPEDTAVYY   100
CASPPGGKLLISLSERISA    120
HHVPMDYWGQGTLVTVSSA    140
SGAELGGGGSGGGGSGGGGS   160
TSQAVLTQPSSASGTPGQRV   180
TISCSGSSSNIGAGYDVHWY   200
QQLPGTAPKLLIYGNSRPS    220
GVPDRFSGSKSGTSASLAIT   240
GLQAEDEADYYCQSYDSSLS   260
AHNYVFGTGTKVTLLG       276
```

Figure 8B

```
  1 MRDLPLTSLA LVLSALGALL GTEALPAEEP AVGTSGLIFR EDLDWPPGSP QEPLCLVALG
 61 GDSNGSSSPL RVVGALSAYE QAFLGAVQRA RWGPRDLATF GVCNTGDRQA ALPSLRRLGA
121 WLRDPGGQRL VVLHLEEVTW EPTPSLRFQE PPPGGAGPPE LALLVLYPGP GPEVTVTRAG
181 LPGAQSLCPS RDTRYLVLAV DPAGAWRGS GLALTLQPEG EDSRLSTARL QALLFGDDHP
241 CFTRMTFALL LLPPSEPAPL PAHGQLDTVP FPPPRPSAEL EESPPSADPF LETLTRLVRA
301 LRVPPARASA PRLALDPDAL AGFPQGLVNL SDPAALERLL DGEEPLLLLL FPTAATTGDP
361 APLHDPTSAP WATALARRVA AELQAAAAEL RSLPGLPPAT APLLARLLAL CPGGPGGLGD
421 PLRALLLLKA LQGLRVEWRG RDPRGPGRAQ RSAGATAADG PCALRELSVD LRAERSVLIP
481 ETYQANNCQG VCGWPQSDRN PRYGNHVVLL LKMQARGAAL ARPPCCVPTA YAGKLLISLS
541 EERTSAHHVP NMVATECGCR
```

Figure 9

```
                         CDR_H1
E3_H            MAQVQLQQSGPGLVKPSQTLSLTCAISGDSVSSKSATWNWIRQSPSRGLE 50
3C2A_H          --EVQLVESGGGLVKPGGSLRLTCVASGFTFS--DYWLNWVRQAPGKGLE 46
                 :***.:**.*****.:*.***..**.:.*  .. **:**:*.:***

3C2A_H_MISlp    --EVQLVESGGGLVKPGGSLRLTCVASGFTFS--DYWLNWVRQAPGKGLE 46
E3_3C2AH3MISlp  MAQVQLQQSGPGLVKPSQTLSLTCAISGDSVSSKSATWNWIRQSPSRGLE 50

CDR_H2
E3_H            WLGRTYYRSK-WYNDYAESVKSRITIKPDTTKNHFSLQLKSVTPEDTAVY 99
3C2A_H          WVGRIKSRTDGGTTDYAASVKGRFTISRDDSKNTLYLQMNSLKTEDTAVY 96
                *:**  *:.    .*** ***.*:**. *.:**  : **::*:..******

3C2A_H_MISlp    WVGRIKSRTDGGTTDYAASVKGRFTISRDDSKNTLYLQMNSLKTEDTAVY 96
E3_3C2AH3MISlp  WLGRTYYRSK-WYNDYAESVKSRITIKPDTTKNHFSLQLKSVTPEDTAVY 99

CDR_H3
E3_H            YCASG----------------------NGYLAYWGQGTLVTVSS 121
3C2A_H          SCTTDGFIMIRGVSED---------YYYYYMDVWGKGTTVTVSS 131
                 *::.                     *:. **:** *.****

MIS_LOOP(lp)            GKLLISLSEERISAHHVP
3C2A_H_MISlp    SCTTDGFIGKLLISLSEERISAHHVPYYYYMDVWGKGTTVTVSS 139
E3_3C2AH3MISlp  YCTTDGFIGKLLISLSEERISAHHVPYYYYMDVWGQGTLVTVSS 142

Alignment symbols:
(*) = identity
(:) = strongly similar properties
(.) = weakly similar properties
```

Figure 10

RATIONALLY-DESIGNED ANTI-MULLERIAN INHIBITING SUBSTANCE TYPE II RECEPTOR ANTIBODIES

This application is a §371 application of PCT/US2012/039831, filed May 29, 2012, which claims priority under 35 U.S.C. §119(e) to U.S. Provisional Patent Application No. 61/490,852, filed May 27, 2011. The foregoing applications are incorporated by reference herein.

FIELD OF THE INVENTION

The present invention relates to the field of immunology. Specifically, compositions and methods for generating hybrid antibodies specific for a protein of interest, particularly the Mullerian inhibiting substance Type II receptor (MISIIR), are disclosed.

BACKGROUND OF THE INVENTION

Several publications and patent documents are cited throughout the specification in order to describe the state of the art to which this invention pertains. Each of these citations is incorporated herein by reference as though set forth in full.

Mullerian inhibiting substance (MIS) is a member of the transforming growth factor-β (TGFβ) superfamily of secreted protein hormones that signal through receptor complexes of type I and type II serine/threonine kinase receptors. The binding of MIS ligand to its receptor initiates a signaling cascade, including phosphorylation of Smad1, that is dependent on recruitment of type I receptors, ALK2 and ALK6, which also signal for bone morphogenetic proteins (Segev et al. (2001) J. Biol. Chem., 276:26799-26806). MIS type II receptor (MISIIR) has been detected on human gynecological cancers (e.g., cervical, ovarian, uterine, vaginal, and vulvar), prostate cancers, and breast cancers (e.g., ductal carcinomas; Segev et al. (2000) J. Biol. Chem., 275:28371-28379; Segev et al. (2001) J. Biol. Chem., 276:26799-26806; Segev et al. (2002) Proc. Natl. Acad. Sci., 99:239-244; Barbie et al. (2003) Proc. Natl. Acad. Sci., 100:15601-15606; Masiakos et al. (1999) Clin. Cancer Res., 5:3488-99; Hoshiya (2003) J. Biol. Chem., 278:51703-12; Hoshiya et al. (2003) Mol. Cell. Endocrinol., 211:43-9; Yuan et al. (2006) Mol. Cancer Ther., 5:2096-105; Song et al. (2009) Int. J. Oncol., 34:1583-91; Bakkum-Gamez et al. (2008) Gynecol. Oncol., 108:141-8). Additionally, the expression of the Simian Virus 40 TAg under Control of the MISIIR Promoter was found to lead to the generation of testicular tumors in transgenic mice, suggesting a role in testicular cancer (Connolly et al. (2003) Cancer Res., 63:1389-97). These findings demonstrate the relevance of MISIIR for anti-cancer therapies.

SUMMARY OF THE INVENTION

In accordance with the present invention, hybrid antibodies which are immunologically specific for Mullerian Inhibiting Substance Type II Receptor (MISIIR) are provided. In a particular embodiment, the hybrid antibody comprises at least one region of Mullerian Inhibiting Substance (MIS) in place of at least one complementarity determining region (CDR). In a particular embodiment, the region of MIS comprises amino acids which have been determined to interact or bind with MISIIR, particularly the extracellular domain of MISIIR. Nucleic acid molecules encoding the antibodies of the instant invention are also encompassed.

In accordance with another aspect of the instant invention, compositions comprising at least one antibody of the instant invention and at least one pharmaceutically acceptable carrier are provided.

In accordance with yet another aspect of the instant invention, methods for inhibiting and/or treating a cancer in a subject are provided. In a particular embodiment, the method comprises administering to a subject in need thereof a therapeutically effective amount of at least one antibody of the instant invention. In a particular embodiment, the antibody is conjugated to at least one radioisotope, chemotherapeutic agent, and/or toxin. The method may further comprise the administration of at least one other cancer therapy such as radiation therapy, surgery to remove the tumor, and/or the administration of at least one other chemotherapeutic agent.

According to another aspect of the instant invention, methods for detecting, imaging, diagnosing, and/or determining an increased risk for cancer in a patient are provided. In a particular embodiment, the methods comprise administering to a patient an antibody of the instant invention. In a particular embodiment, the antibody comprises at least one detectable label. The instant invention also encompasses methods for detecting the presence of MISIIR in a biological sample. In a particular embodiment, the method comprises incubating a biological sample with at least one antibody of the instant invention, optionally comprising at least one detectable label.

In accordance with yet another aspect of the instant invention, methods for generating a hybrid antibody immunologically specific for a target protein are provided. In a particular embodiment, the method comprises replacing at least one complementarity determining region (CDR) of an antibody with at least one amino acid sequence from a ligand of the target protein.

BRIEF DESCRIPTIONS OF THE DRAWING

FIG. 1 provides a schematic model of the interaction between MISIIR (left) and MIS (right).

Figure 2:

FIG. 2 provides a model of the interaction between hybrid MIS-mAb with MISIIR.

Figure 3:
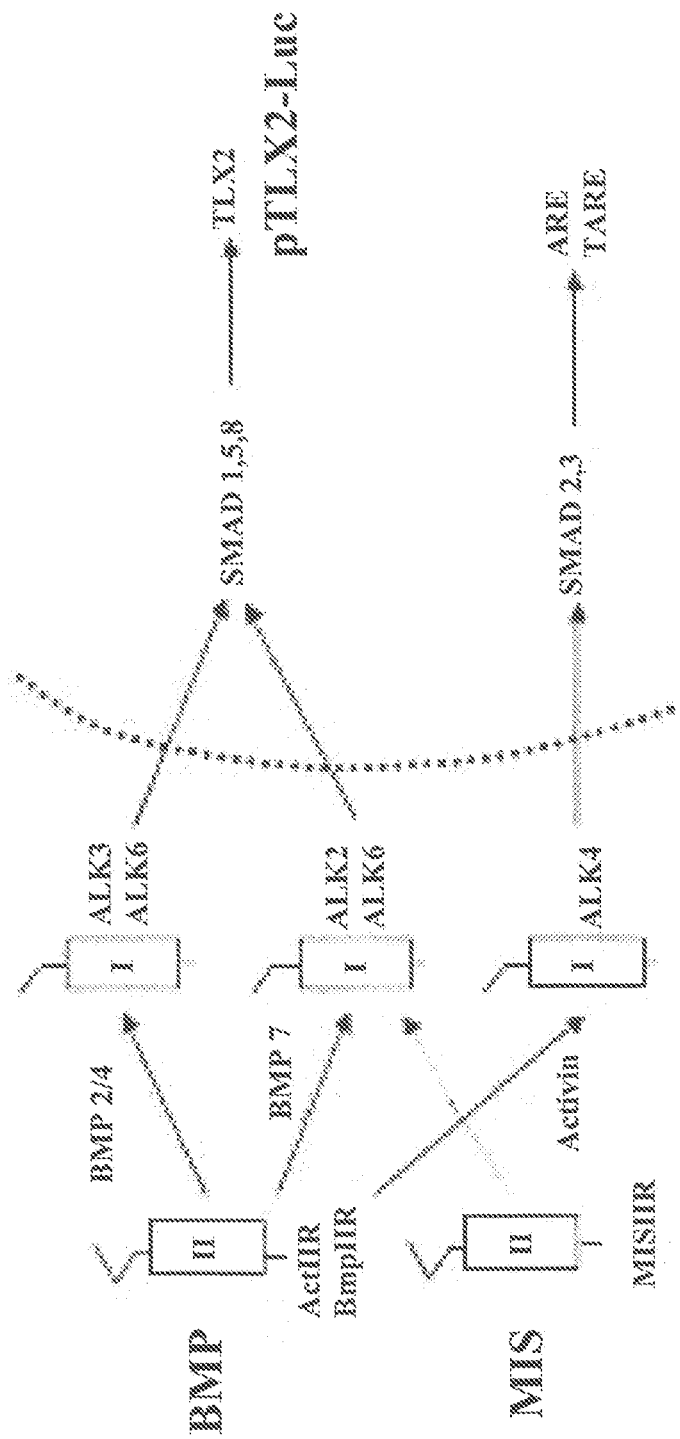

FIG. 3 provides a schematic of a reporter gene assay to measure MISIIR signaling. The Tlx-2 (T-cell leukemia, homeobox 2) gene is a downstream target of BMP and MIS signaling (Tang et al. (1998) Development 125:1877-1887). Genes encoding mouse TLX2-luciferase and human MISIIR were stably transfected into P19 mouse neuroblastoma cells that normally lack MISIIR.

Figure 4:
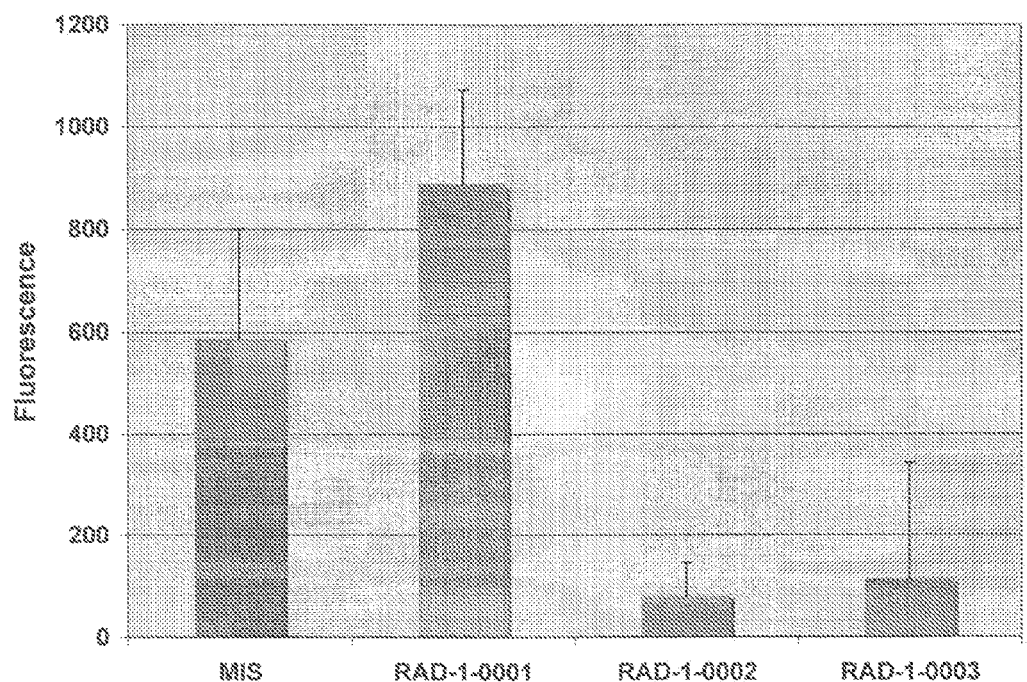

FIG. 4 provides a graph showing MIS signal modulation by scFv MIS mimetics.

FIGS. 5A and 5B provide the nucleotide sequence of the E3 parent scFV with (SEQ ID NO: 6) and without (SEQ ID NO: 1) a histidine tag, respectively. Nucleotides in bold uppercase letters represent the CDR3 loops of the heavy and light chains.

FIGS. 6A and 6B provide the nucleotide (SEQ ID NO: 2) and amino acid (SEQ ID NO: 7) sequences, respectively, of RAD-1-0001 (E3 3C2AH3) scFV, without the His tag. Bold uppercase letters are changed from parental E3 scFv.

FIGS. 7A and 7B provide the nucleotide (SEQ ID NO: 3) and amino acid (SEQ ID NO: 8) sequences, respectively, of RAD-1-0002 (E3 1AQKL3) scFv, without the His tag. Bold uppercase letters are changed from parental E3 scFv.

FIGS. 8A and 8B provide the nucleotide (SEQ ID NO: 4) and amino acid (SEQ ID NO: 9) sequences, respectively, of RAD-1-0003 (E3 1DQH3) scFv, without the His tag. Bold uppercase letters are changed from parental E3 scFv.

FIG. 9 provides an amino acid sequence (SEQ ID NO: 5) for human MIS.

FIG. 10 provides a sequence alignment of the heavy chains of E3 (SEQ ID NO: 10) and 3C2A (SEQ ID NO: 11). The structure of the antibody 3C2A, which shares many identical residues with E3, is available in the Protein Data Bank (PDB, www.rcsb.org). During modeling, the MIS-loop (SEQ ID NO: 12) was introduced into the 3C2A heavy chain (3C2A_H). To make space for the residues of the MIS-loop, some of the residues of the CDR_H3 of 3C2A_H (3C2AH3) were removed (MIRGVSEDYY; SEQ ID NO; 13). This sequence was replaced by the MIS-loop, giving rise to the MIS-modified CDRH3 of 3C2A_H (3C2A_H_MISlp). Lastly, the sequence of the CDR_H3 of 3C2A_H_MISlp (TT . . . DV) was introduced into the heavy chain of E3 (E3_H), thus creating the E3-based heavy chain (E3_3C2AH3MISlp or E3_3C2AH3).

DETAILED DESCRIPTION OF THE INVENTION

In accordance with the present invention, methods for generating hybrid antibodies specific for a protein of interest, particularly MISIIR, are provided. The methods comprise replacing at least one complementarity determining region (CDR; e.g., CDR1, CDR2, or CDR3 of the heavy or light chain) of an antibody or antibody fragment with at least one amino acid sequence from a protein which binds the protein of interest. For example, at least one complementarity determining region of an antibody or antibody fragment can be replaced with a portion of a ligand that is involved in the binding of the ligand (e.g., a loop) to the protein of interest (e.g. the ligand's receptor). The resultant hybrid antibody specifically binds (is immunologically specific for) the protein of interest.

In accordance with another aspect of the instant invention, hybrid anti-MISIIR antibodies and methods of use thereof are provided. Specifically, methods for the immunodetection and imaging of cancer associated with MISIIR expression and methods of treating the same are provided.

I. Hybrid Antibody Molecules

The instant invention provides methods for generating hybrid antibodies or antibody fragments which specifically bind a target protein. In a particular embodiment, the method comprises replacing at least one complementarity determining region (CDR) in an antibody or antibody fragment with at least one amino acid sequence from a ligand of the target protein. A skilled artisan can readily identify the CDRs of an antibody or antibody fragment (see, e.g., www.bioinf.org.uk/abs/). In a particular embodiment, the method comprises replacing the CDR3 of the heavy chain and/or the CDR3 of the light chain of the antibody or antibody fragment.

The framework antibody (the antibody that has at least one CDR replaced) can be any antibody, antibody fragment, antibody-containing protein/polypeptide, or antibody mimic. In a particular embodiment, the framework antibody is a monoclonal antibody. The framework antibody may be naturally occurring or may be a synthetic antibody (e.g., a recombinantly generated antibody; a chimeric antibody; a bispecific antibody; a humanized antibody; a camelid antibody; and the like). The framework antibody may comprise at least one purification tag. In a particular embodiment, the framework antibody is an antibody fragment. Antibody fragments include, without limitation, immunoglobulin fragments including, without limitation: single domain (Dab; e.g., single variable light or heavy chain domain), Fab, Fab', F(ab')$_2$, and F(v); and fusions (e.g., via a linker) of these immunoglobulin fragments including, without limitation: scFv, scFv$_2$, scFv-Fc, minibody, diabody, triabody, and tetrabody. The framework antibody may also be a protein (e.g., a fusion protein) comprising at least one antibody or antibody fragment. The framework antibody may also be a synthetic protein which mimics an immunoglobulin. Examples include, without limitation, Affibody® molecules (Affibody, Bromma, Sweden), darpins (designed ankyrin repeat proteins; Kawe et al. (2006) J. Biol. Chem., 281: 40252-40263), and peptabodies (Terskikh et al. (1997) PNAS 94:1663-1668). In a particular embodiment of the instant invention, the framework antibody is an scFv.

"Fv" is an antibody fragment which contains an antigen-recognition and -binding site. This region consists of a dimer of one heavy- and one light-chain variable domain in tight, non-covalent association. It is in this configuration that the three CDRs of each variable domain interact to define an antigen-binding site on the surface of the $V_H$-$V_L$ dimer. Collectively, the six CDRs confer antigen-binding specificity to the antibody. However, even a single variable domain (or half of an Fv comprising only three CDRs specific for an antigen) has the ability to recognize and bind antigen, although often at a lower affinity than the entire binding site.

"Single-chain Fv" or "scFv" antibody fragments comprise the $V_H$ and $V_L$ domains of an antibody, wherein these domains are present in a single polypeptide chain. Generally, the Fv polypeptide further comprises a polypeptide linker between the $V_H$ and $V_L$ domains which enables the scFv to form the desired structure for antigen binding.

The framework antibody may be immunologically specific for the protein of interest or may be immunologically specific for a different protein (i.e., the framework antibody may have little or no affinity for the target protein prior to manipulation by the methods of the instant invention). In a particular embodiment, the framework antibody has at least 30%, 40%, 50%, 60%, 70%, 75%, 80%, 85%, 90%, 95%, 98% or more homology (identity) with the antibody encoded by SEQ ID NO: 1. In a particular embodiment, the framework antibody has amino acid sequence encoded by SEQ ID NO: 1 or 6.

As stated hereinabove, the methods of the instant invention may comprise replacing at least one complementarity determining region (CDR) in the framework antibody with an amino acid sequence from a ligand of the target protein. In a particular embodiment, more than one CDR is replaced. The use of multiple CDRs can further stabilize the interaction with the target. In a particular embodiment, multiple CDRs are replaced with ligands of more than one target protein, thereby generating hybrid antibodies which are specific for more than one target protein (e.g., bispecific).

While the CDR of the framework antibody may be replaced, the methods of the instant invention also encompass the insertion of at least one ligand sequence into the existing CDR of the framework antibody. In a particular embodiment, at least one amino acid or at least 1%, 5%, 10%, 20%, 30%, 40%, 50%, 60%, 70%, 80%, 85%, 90%, 95%, 98%, or all of the CDR is replaced with at least one amino acid sequence from a ligand of the target protein. In a particular embodiment, the CDR is between about 5 and about 30 amino acids in length, particularly about 5 to about 15 amino acids in length. In a particular embodiment, the amino sequence from the ligand comprises amino acids which have been determined (e.g., through computer modeling or mutational screening analyses) to interact with the protein of interest.

The inserted amino acid sequence need not be the same length as the CDR segment being removed from the framework antibody. In a particular embodiment, the framework antibody may be modified (e.g., shortened or lengthened) to properly orient and/or stabilize the inserted loop. The framework antibody may also be modified to add more interactive residue positions than the CDR can accommodate. The inserted amino acid sequence may comprise one contiguous sequence of the ligand or may comprise more than one region of contiguous amino acids from the ligand. For example, multiple regions (e.g., about 5 to about 25 amino acids in length), optionally separated by a linker, of the ligand thought to interact with the target protein may be inserted into one CDR. The inserted amino acid sequence may comprise from 1 to about 100 amino acids of the ligand, more particularly about 5 to about 50 amino acids or about 10 to about 50 amino acids. The insertion into the framework antibody may comprise linker regions on one or both ends of the sequence from the ligand (e.g., to provide for proper orientation of the ligand sequence). In a particular embodiment, the linker regions may be about 1 to about 20 amino acids, particularly about 1 to about 10 amino acids.

In a particular embodiment of the instant invention, the target protein is MISIIR (also known as AMHR2 (anti-Mullerian hormone receptor, type II); GenBank GeneID: 269; GenBank Accession Nos. NP_065434 and NM_020547). At least one CDR (e.g., at least one CDR3) of a framework antibody (e.g., E3 or 3C2A) may be replaced by a region of MIS (also known as AMH (anti-Mullerian hormone); GenBank GeneID: 268). In a particular embodiment, regions of MIS comprising amino acids determined to be involved in the interaction of MIS (e.g., cleaved MIS (see Pepinsky et al. (1988) J. Biol. Chem., 263:18961-18964) with MISIIR can be inserted into the framework antibody. FIG. 9 provides an example amino acid sequence for uncleaved human MIS (SEQ ID NO: 5). The amino acid sequence to be inserted into the framework antibody may comprise amino acids determined to interact with the extracellular domain of MISIIR, particularly the MIS binding sites. In a particular embodiment, the amino acid sequence to be inserted into the framework antibody comprises all or part of amino acids 533-550 of SEQ ID NO: 5. In another embodiment, the amino acid sequence to be inserted into the framework antibody comprises all or part of amino acids 466-486 of SEQ ID NO: 5.

The instant invention encompasses the hybrid antibodies generated by the above methods. The instant invention also encompasses MISIIR antibodies having at least 30%, 40%, 50%, 60%, 70%, 75%, 80%, 85%, 90%, 95%, 98%, or 100% homology with SEQ ID NOs: 7, 8, or 9 or those encoded by SEQ ID NOs: 2, 3, or 4 (with or without His tag).

The MISIIR antibodies of the instant invention may be further modified to increase specificity or binding affinity for MISIIR. For example, in the context of E3 3C2AH3 (SEQ ID NO: 7), at least one of K109, E117, R118, I119, and A121 is changed to a different amino acid. In a particular embodiment, the new amino acid is a conservative change. In a particular embodiment, at least one of K109, R118, and A121 is changed to a different amino acid. Specific examples of substitutions include K109R, E117G, R118N, R118D, I119P, and A121L. Notably, the mutation at I119 does not directly face MISIIR, but would relax the loop hairpin, thereby allowing for better binding. As stated hereinabove, the numbering of the mutations is in the context of E3 3C2AH3, but corresponding mutations in the antibody or MIS loop can be made in antibodies having different frameworks (e.g., by using an alignment (see FIG. 10) or computer modeling).

Once bound with MIS, MISIIR heterodimerizes with type I receptors (see, e.g., FIG. 3). The MISIIR antibodies of the instant invention may be further modified to add specificity for a type I receptor (e.g., ALK2). For example, in the context of E3 3C2AH3 (SEQ ID NO: 7), at least one of L111, S113, S120, H122, V124, P125, and Y126 is changed to a different amino acid. In a particular embodiment, the new amino acid is a conservative change. In a particular embodiment, at least one of L111, S113, S120, and V124 is changed to a different amino acid. Specific examples of substitutions include L111M, S113Y, S120V, H122K, H122R, V124Y, P125R, and Y126F. The numbering of the mutations is in the context of E3 3C2AH3, but corresponding mutations in the antibody or MIS loop can be made in antibodies having different frameworks (e.g., by using an alignment (see FIG. 10) or computer modeling).

The antibodies of the instant invention may comprise one or more of the mutations described above. In a particular embodiment, the antibody comprises at least one mutation to increase specificity for MISIIR and at least one mutation to increase specificity for a type I receptor.

The generated antibodies of the instant invention may be further modified. For example, the hybrid antibodies may be humanized. In a particular embodiment, the hybrid antibodies (or a portion thereof) are inserted into the backbone of an antibody or antibody fragment construct. For example, the variable light domain and/or variable heavy domain of the hybrid MISIIR scFv antibodies of the instant invention (e.g., the regions on either side of the $(G_4S)_3$ linker) may be inserted into another antibody construct. Methods for recombinantly producing antibodies are well-known in the art. Indeed, commercial vectors for certain antibody and antibody fragment constructs are available.

The hybrid antibodies of the instant invention may also be conjugated/linked to other components. For example, the hybrid antibodies may be operably linked (e.g., covalently linked, optionally, through a linker) to at least one detectable agent, imaging agent, contrast agent, chemotherapeutic agent, cytotoxic molecule (e.g., immunotoxin), cytokine, and/or any other biological compound. The hybrid antibodies of the instant invention may also comprise at least one purification tag (e.g., a His-tag). The hybrid antibodies of the instant invention may also be linked to other antibodies (e.g., to generate scFv-scFv). For example, the hybrid antibodies of the instant invention may be linked to another antibody to generate bispecific antibodies. The antibodies may be linked together as a fusion protein, optionally via a linker domain (e.g., from about 1 to about 100 amino acids). The antibodies may be linked together via a carrier molecule (e.g., human serum albumin. The antibodies may also be linked together via "knobs into holes" engineering (e.g., preferentially pairing of light and heavy chains; see, e.g., Ridgway et al. (1996) Protein Eng. (1996) 9:617-621).

Compositions comprising the hybrid antibodies are also encompassed by the instant invention. In a particular embodiment, the composition comprises at least one hybrid antibody of the instant invention and at least one pharmaceutically acceptable carrier.

The methods of the instant invention may further comprise assaying the hybrid antibodies for their ability to bind the target protein (e.g., ELISA).

The antibody molecules of the invention may be prepared using a variety of methods known in the art. Antibodies may be prepared by chemical cross-linking, hybrid hybridoma techniques and by expression of recombinant antibody or antibody fragments expressed in host cells, such as mammalian cells, bacteria or yeast cells. In one embodiment of the invention, the antibody molecules are produced by expression of recombinant antibody or antibody fragments in host cells. The nucleic acid molecules encoding the hybrid antibody may be inserted into expression vectors and introduced into host cells. The resulting antibody molecules are then isolated and purified from the expression system. The antibodies optionally comprise a purification tag by which the antibody can be purified.

The purity of the antibody molecules of the invention may be assessed using standard methods known to those of skill in the art, including, but not limited to, ELISA, immunohistochemistry, ion-exchange chromatography, affinity chromatography, immobilized metal affinity chromatography (IMAC), size exclusion chromatography, polyacrylamide gel electrophoresis (PAGE), western blotting, surface plasmon resonance and mass spectroscopy.

II. Uses Of Anti-Misiir Antibody Molecules

Anti-MISIIR antibodies have broad applications in therapy and diagnosis. Specifically, the anti-MISIIR antibody molecules of the invention may be used, for example: (1) to directly alter the growth of tumors that express MISIIR; (2) to alter the growth of tumors that express MISIIR in combination with other cytotoxic/chemotherapeutic agents; (3) to image tumors that express MISIIR; (4) as a diagnostic tool; and (5) to directly improve the survival of damaged nerves (e.g., motor neurons) that express MISIIR (Wang et al. (PNAS (2005) 102:16421-16425).

1) The anti-MISIIR antibody molecules of the instant invention can be administered to a patient in need thereof, as described hereinbelow. The anti-MISIIR antibody molecules may be delivered to a subject to inhibit or treat cancer. In a particular embodiment, the cancer expresses MISIIR. In a particular embodiment, the cancer is cervical, ovarian, uterine, vaginal, vulvar, prostate, breast, or testicular. The anti-MISIIR antibody molecules of the instant invention include the antibodies alone and antibodies conjugated to other agents such as, without limitation, cytotoxic molecules, chemotherapeutic agents, radioisotopes, pro-drugs, pro-drug activating enzymes capable of converting a pro-drug to its active form, and magnetic beads (see, for example, U.S. Pat. No. 6,645,731). If the compound to be conjugated is proteinaceous, a fusion protein may be generated with the antibody molecule. Radiosensitizers may also be administered with the antibodies.

2) To alter the growth of tumors that express MISIIR, the anti-MISIIR antibody molecules of the instant invention may be administered to a patient in combination with other cytotoxic agents. These other cytotoxic agents include, without limitation, chemotherapeutic agents, radiation therapy (e.g., external beam radiation), targeted radioisotopes, and other antibodies or signal transduction inhibitors. Radiosensitizers may also be administered with the antibodies.

3) When employed for imaging tumors, the anti-MISIIR antibody molecules of the invention can be conjugated to radioisotopes, imaging agent, and/or contrast agent as described hereinabove. The anti-MISIIR antibody molecules can be conjugated to the radioisotopes by any method including direct conjugation and by linking through a chelator (see, for example, U.S. Pat. No. 4,624,846). The anti-MISIIR antibody molecules may also be conjugated to labels or contrast agents such as, without limitation, paramagnetic or superparamagnetic ions for detection by MRI imaging and optical and fluorescence and/or mammography agents (examples of other labels are provided in, for example, U.S. Pat. Nos. 3,817,837; 3,850,752; 3,939,350; 3,996,345; 4,277,437; 4,275,149 and 4,366,241). Paramagnetic ions include, without limitation, Gd(III), Eu(III), Dy(III), Pr(III), Pa(IV), Mn(II), Cr(III), Co(III), Fe(III), Cu(II), Ni(II), Ti(III), and V(IV). Fluorescent agents include, without limitation, fluorescein and rhodamine and their derivatives. Optical agents include, without limitation, derivatives of phorphyrins, anthraquinones, anthrapyrazoles, perylenequinones, xanthenes, cyanines, acridines, phenoxazines and phenothiazines. Mammography agents include, without limitation, derivatives of iodine or metals such as gold, gold particles or gold nanoparticles.

In an alternative method, a secondary binding ligand, such as a second antibody or a biotin/avidin ligand binding arrangement, which can recognize the anti-MISIIR antibody molecules of the instant invention, may be conjugated with the agents described above instead of with the anti-MISIIR antibody molecules. The conjugated secondary binding ligand can then be used in conjunction with anti-MISIIR antibody molecules in any of the assays described herein.

4) The anti-MISIIR antibody molecules of the invention may be used to 1) diagnose (e.g., determine an increased risk of) cancer in patient, 2) determine the prognosis of a patient, including stage and grade (particularly whether it is metastatic) of a tumor and its potential sensitivity to therapy, 3) determine the origin of a tumor, 4) determine the efficacy of a treatment of a patient. In one embodiment the anti-MISIIR antibody molecules are utilized to detect the presence of MISIIR in a biological sample from a patient. The biological sample may include biopsies of various tissues including, without limitation: breast, prostate, cervical, ovarian, testicular, and pulmonary. Cellular examples of biological samples include tumor cells, blood cells, ovarian cells, prostate cells, breast cells, testicular cells, cervical cells, and lung cells. The biological sample may also be a biological fluid, wherein shed MISIIR can be detected, such as, without limitation, blood, serum, nipple aspirate and urine. Many immunological assays are well known in the art for assaying of biological samples for the presence of a certain protein including, without limitation: immunoprecipitations, radioimmunoassays, enzyme-linked immunosorbent assays (ELISA), immunohistochemical assays, Western blot and the like.

The presence of MISIIR in fluids such as blood may be indicative of the presence of cancer. The presence of MISIIR in fluids or sites not near the tumor may be indicative of metastases. The loss of MISIIR expression in a patient, particularly one undergoing treatment, over time may be indicative of remission (i.e., successful treatment), while the lack of change in MISIIR levels in a patient undergoing treatment may be indicative of resistance to the therapy and my indicate that a different therapeutic strategy could be employed. Similarly, the gain of MISIIR expression in a patient over time can be indicative of recurrence. Additionally, the imaging techniques described hereinabove may be employed to monitor the size of the tumor to determine the efficacy of a treatment. In a particular embodiment of the invention, other cancer diagnostic assays can be performed to confirm the results obtained with the instant invention.

5) The anti-MISIIR antibodies of the instant invention may be administered to a subject to improve the survival of damaged nerves (e.g., motor neurons). In a particular embodiment, the subject has a motor neuron disease. The instant invention encompasses methods of inhibiting or treating a neuropathy (any disease, disorder, or injury of the nerves) in a subject (particularly a motor neuron disease or motor neuropathy), comprising the administration of the anti-MISIIR antibody molecules of the invention.

The anti-MISIIR antibody molecules of the invention may also be used in gene therapy for direct targeting of vehicles (liposomes, viruses etc.) containing genes to specific tumors expressing MISIIR. In an exemplary embodiment, liposomes may be studded by the anti-MISIIR antibody molecules of the invention to facilitate tumor specific targeting. In another embodiment, anti-MISIIR antibodies may be expressed directly on the surface of viruses or as fusions with viral coat proteins to facilitate tumor specific targeting. The genes targeted in this manner can have a direct antitumor effect, sensitize the tumor to other agents or increase the susceptibility of the tumor to a host immune response. Anti-cancer agents such as chemotherapeutic agents, toxins, antibodies, antisense molecules, RNAi and/or radioisotopes may also be encapsulated in liposomes, or other nanoparticles known to ones skilled in the art, so modified.

In another embodiment, the anti-MISIIR antibody molecules may be used to direct gene therapy vectors, including but not limited to modified viruses, to cells that express MISIIR. Viruses and other vectors may also be utilized to deliver the genes for the anti-MISIIR antibody molecules to tumor cells where they could be produced and secreted into the cellular microenvironment or, through the addition of additional intracellular targeting sequences, they could be turned into intrabodies that localize to specific cellular compartments and knockout the expression of their targets.

In yet another embodiment of the instant invention, the anti-MISIIR antibody molecules of the instant invention can be conjugated or covalently attached to another targeting agent to increase the specificity of the tumor targeting or alter signal transduction through a more than one receptor (e.g., MISIIR and MISIR (e.g., ALK2, ALK3, ALK6)). Targeting agents can include, without limitation, antibodies, hybrid antibodies described herein, alternate scaffolds (e.g., affibodies, darpins, etc.), cytokines, and receptor ligands. In a particular embodiment, the targeting agent is overexpressed on the tumor as compared to normal tissue. Additionally, the anti-MISIIR antibody molecules of the instant invention can be conjugated or covalently attached to compounds which elicit an immune response such as, without limitation, cytokines.

The present invention further encompasses kits for use in detecting the expression of MISIIR in biological samples. Such kits may comprise the anti-MISIIR antibody molecules of the invention specific for MISIIR (particularly in at least one carrier) as well as buffers and other compositions and instruction material to be used for the detection of the MISIIR.

The antibodies as described herein will generally be administered to a patient as a pharmaceutical preparation. The term "patient" as used herein refers to human or animal subjects. These antibodies may be employed therapeutically, under the guidance of a physician for the treatment of malignant tumors and metastatic disease.

The pharmaceutical preparation comprising the antibody molecules of the invention may be conveniently formulated for administration with at least one pharmaceutically acceptable carrier, such as water, buffered saline, ethanol, polyol (for example, glycerol, propylene glycol, liquid polyethylene glycol and the like), dimethyl sulfoxide (DMSO), oils, detergents, suspending agents or suitable mixtures thereof. The concentration of antibody molecules in the chosen medium will depend on the hydrophobic or hydrophilic nature of the medium, as well as the size and other properties of the antibody molecules. Solubility limits may be easily determined by one skilled in the art.

As used herein, "pharmaceutically acceptable carrier" includes any and all solvents, dispersion media and the like which may be appropriate for the desired route of administration of the pharmaceutical preparation, as exemplified in the preceding paragraph. The use of such media for pharmaceutically active substances is known in the art. Except insofar as any conventional media or agent is incompatible with the antibody molecules to be administered, its use in the pharmaceutical preparation is contemplated.

The dose and dosage regimen of an antibody according to the invention that is suitable for administration to a particular patient may be determined by a physician considering the patient's age, sex, weight, general medical condition, and the specific condition and severity thereof for which the antibody is being administered. The physician may also consider the route of administration of the antibody, the pharmaceutical carrier with which the antibody may be combined, and the antibody's biological activity.

Selection of a suitable pharmaceutical preparation depends upon the method of administration chosen. For example, the antibodies of the invention may be administered by direct injection into any cancerous tissue or into the area surrounding the cancer or damaged nerve. In this instance, a pharmaceutical preparation comprises the antibody molecules dispersed in a medium that is compatible with the cancerous tissue or the damaged nerve tissue.

Antibodies may also be administered parenterally by intravenous injection into the blood stream, or by subcutaneous, intramuscular, intrathecal, or intraperitoneal injection. Pharmaceutical preparations for parenteral injection are known in the art. If parenteral injection is selected as a method for administering the antibodies, steps must be taken to ensure that sufficient amounts of the molecules reach their target cells to exert a biological effect. The lipophilicity of the antibodies, or the pharmaceutical preparation in which they are delivered, may have to be increased so that the molecules can arrive at their target locations. Furthermore, the antibodies may have to be delivered in a cell-targeting carrier so that sufficient numbers of molecules will reach the target cells. Methods for increasing the lipophilicity of a molecule are known in the art. If a small form of the antibody is to be administered, including but not limited to a Fab fragment, a Dab, an scFv or a diabody, it may be conjugated to a second molecule such as, but not limited to polyethylene glycol (PEG) or an albumin-binding antibody or peptide to prolong its retention in blood.

Pharmaceutical compositions containing a compound of the present invention as the active ingredient in intimate admixture with a pharmaceutical carrier can be prepared according to conventional pharmaceutical compounding techniques. The carrier may take a wide variety of forms depending on the form of preparation desired for administration, e.g., intravenous, oral or parenteral. In preparing the antibody in oral dosage form, any of the usual pharmaceutical media may be employed, such as, for example, water, glycols, oils, alcohols, flavoring agents, preservatives, coloring agents and the like in the case of oral liquid preparations (such as, for example, suspensions, elixirs and solutions); or carriers such as starches, sugars, diluents, granulating agents, lubricants, binders, disintegrating agents and the like in the case of oral solid preparations (such as, for example, powders, capsules and tablets). Because of their ease in administration, tablets and capsules represent the most advantageous oral dosage unit form in which case solid pharmaceutical carriers are obviously employed. If desired, tablets may be sugar-coated or enteric-coated by standard techniques. For parenterals, the carrier will usually comprise sterile water, though other ingredients, for example, to aid solubility or for preservative purposes, may be included. Injectable suspensions may also be prepared, in which case appropriate liquid carriers, suspending agents and the like may be employed.

A pharmaceutical preparation of the invention may be formulated in dosage unit form for ease of administration and uniformity of dosage. Dosage unit form, as used herein, refers to a physically discrete unit of the pharmaceutical preparation appropriate for the patient undergoing treatment. Each dosage should contain a quantity of active ingredient calculated to produce the desired effect in association with the selected pharmaceutical carrier. Procedures for determining the appropriate dosage unit are well known to those skilled in the art.

Dosage units may be proportionately increased or decreased based on the weight of the patient. Appropriate concentrations for alleviation of a particular pathological condition may be determined by dosage concentration curve calculations, as known in the art.

In accordance with the present invention, the appropriate dosage unit for the administration of anti-MISIIR antibody molecules may be determined by evaluating the toxicity of the antibody molecules in animal models. Various concentrations of antibody pharmaceutical preparations may be administered to mice with transplanted human tumors, and the minimal and maximal dosages may be determined based on the results of significant reduction of tumor size and side effects as a result of the treatment. Appropriate dosage unit may also be determined by assessing the efficacy of the antibody molecule treatment in combination with other standard anti-cancer drugs. The dosage units of anti-MISIIR antibody molecules may be determined individually or in combination with each anti-cancer treatment according to greater shrinkage and/or reduced growth rate of tumors.

The pharmaceutical preparation comprising the anti-MISIIR antibody molecules may be administered at appropriate intervals, for example, at least twice a day or more until the pathological symptoms are reduced or alleviated, after which the dosage may be reduced to a maintenance level. The appropriate interval in a particular case would normally depend on the condition of the patient.

III. Definitions

The following definitions are provided to facilitate an understanding of the present invention: "Nucleic acid" or a "nucleic acid molecule" as used herein refers to any DNA or RNA molecule, either single or double stranded and, if single stranded, the molecule of its complementary sequence in either linear or circular form. In discussing nucleic acid molecules, a sequence or structure of a particular nucleic acid molecule may be described herein according to the normal convention of providing the sequence in the 5' to 3' direction. With reference to nucleic acids of the invention, the term "isolated nucleic acid" is sometimes used. This term, when applied to DNA, refers to a DNA molecule that is separated from sequences with which it is immediately contiguous in the naturally occurring genome of the organism in which it originated. For example, an "isolated nucleic acid" may comprise a DNA molecule inserted into a vector, such as a plasmid or virus vector, or integrated into the genomic DNA of a prokaryotic or eukaryotic cell or host organism. An isolated nucleic acid (either DNA or RNA) may further represent a molecule produced directly by biological or synthetic means and separated from other components present during its production.

A "vector" is a nucleic acid molecule such as a plasmid, cosmid, bacmid, phage, or virus, to which another genetic sequence or element (either DNA or RNA) may be attached so as to bring about the replication of the attached sequence or element.

An "expression operon" refers to a nucleic acid segment that may possess transcriptional and translational control sequences, such as promoters, enhancers, translational start signals (e.g., ATG or AUG codons), polyadenylation signals, terminators, and the like, and which facilitate the expression of a polypeptide coding sequence in a host cell or organism.

The term "substantially pure" refers to a preparation comprising at least 50-60% by weight of a given material (e.g., nucleic acid, oligonucleotide, polypeptide, protein, etc.). More preferably, the preparation comprises at least 75% by weight, and most preferably 90-95% by weight of the given compound. Purity is measured by methods appropriate for the given compound (e.g. chromatographic methods, agarose or polyacrylamide gel electrophoresis, HPLC analysis, and the like).

The term "isolated protein" or "isolated and purified protein" is sometimes used herein. This term refers primarily to a protein produced by expression of an isolated nucleic acid molecule of the invention. Alternatively, this term may refer to a protein that has been sufficiently separated from other proteins with which it would naturally be associated, so as to exist in "substantially pure" form. "Isolated" is not meant to exclude artificial or synthetic mixtures with other compounds or materials, or the presence of impurities that do not interfere with the fundamental activity, and that may be present, for example, due to incomplete purification, addition of stabilizers, or compounding into, for example, immunogenic preparations or pharmaceutically acceptable preparations.

The phrase "operably linked," as used herein, may refer to a nucleic acid or amino acid sequence placed into a functional relationship with another nucleic acid or amino acid sequence. Examples of nucleic acid sequences that may be operably linked include, without limitation, promoters, cleavage sites, purification tags, transcription terminators, enhancers or activators and heterologous genes which when transcribed and translated will produce a functional product such as a protein, ribozyme or RNA molecule.

An "antibody" or "antibody molecule" is any immunoglobulin, including antibodies and fragments thereof, that binds to a specific antigen. As used herein, antibody or antibody molecule contemplates intact immunoglobulin molecules, immunologically active portions of an immunoglobulin molecule, and fusions of immunologically active portions of an immunoglobulin molecule.

As used herein, the term "immunologically specific" refers to proteins/polypeptides, particularly antibodies, that bind to one or more epitopes of a protein or compound of interest, but which do not substantially recognize and bind other molecules in a sample containing a mixed population of antigenic biological molecules.

As used herein, the term "immunotoxin" refers to chimeric molecules in which antibody molecules or fragments thereof are coupled or fused (i.e., expressed as a single polypeptide or fusion protein) to toxins or their subunits. Toxins to be conjugated or fused can be derived form various sources, such as plants, bacteria, animals, and humans or be synthetic toxins (drugs), and include, without limitation, saprin, ricin, abrin, ethidium bromide, diptheria toxin, Pseudomonas exotoxin, PE40, PE38, saporin, gelonin, RNAse, protein nucleic acids (PNAs), ribosome inactivating protein (RIP), type-1 or type-2, pokeweed antiviral protein (PAP), bryodin, momordin, and bouganin.

The term "conjugated" refers to the joining by covalent or noncovalent means of two compounds or agents of the invention.

Chemotherapeutic agents are compounds that exhibit anticancer activity and/or are detrimental to a cell (e.g., a toxin). Suitable chemotherapeutic agents include, but are not limited to: toxins (e.g., saporin, ricin, abrin, ethidium bromide, diptheria toxin, Pseudomonas exotoxin, and others listed above; thereby generating an immunotoxin when conjugated or fused to an antibody); alkylating agents (e.g., nitrogen mustards such as chlorambucil, cyclophosphamide, isofamide, mechlorethamine, melphalan, and uracil mustard; aziridines such as thiotepa; methanesulphonate esters such as busulfan; nitroso ureas such as carmustine, lomustine, and streptozocin; platinum complexes such as cisplatin and carboplatin; bioreductive alkylators such as mitomycin, procarbazine, dacarbazine and altretamine); DNA strand-breakage agents (e.g., bleomycin); topoisomerase II inhibitors (e.g., amsacrine, dactinomycin, daunorubicin, idarubicin, mitoxantrone, doxorubicin, etoposide, and teniposide); DNA minor groove binding agents (e.g., plicamydin); antimetabolites (e.g., folate antagonists such as methotrexate and trimetrexate; pyrimidine antagonists such as fluorouracil, fluorodeoxyuridine, CB3717, azacitidine, cytarabine, and floxuridine; purine antagonists such as mercaptopurine, 6-thioguanine, fludarabine, pentostatin; asparginase; and ribonucleotide reductase inhibitors such as hydroxyurea); tubulin interactive agents (e.g., vincristine, vinblastine, and paclitaxel (Taxol)); hormonal agents (e.g., estrogens; conjugated estrogens; ethinyl estradiol; diethylstilbesterol; chlortrianisen; idenestrol; progestins such as hydroxyprogesterone caproate, medroxyprogesterone, and megestrol; and androgens such as testosterone, testosterone propionate, fluoxymesterone, and methyltestosterone); adrenal corticosteroids (e.g., prednisone, dexamethasone, methylprednisolone, and prednisolone); leutinizing hormone releasing agents or gonadotropin-releasing hormone antagonists (e.g., leuprolide acetate and goserelin acetate); and antihormonal antigens (e.g., tamoxifen, antiandrogen agents such as flutamide; and antiadrenal agents such as mitotane and aminoglutethimide). Preferably, the chemotheraputic agent is selected from the group consisting of: placitaxel (Taxol®), cisplatin, docetaxol, carboplatin, vincristine, vinblastine, methotrexate, cyclophosphamide, CPT-11, 5-fluorouracil (5-FU), gemcitabine, estramustine, carmustine, adriamycin (doxorubicin), etoposide, arsenic trioxide, irinotecan, and epothilone derivatives.

The term "pro-drug" refers to a compound which is transformed in vivo to an active form of the drug. The pro-drug may be transformed to an active form only upon reaching the target in vivo or upon internalization by the target cell.

Radioisotopes of the instant invention include, without limitation, positron-emitting isotopes and alpha-, beta-, gamma-, Auger- and low energy electron-emitters. The radioisotopes include, without limitation: $^{13}$N, $^{18}$F, $^{32}$P, $^{64}$Cu, $^{66}$Ga, $^{67}$Ga, $^{68}$Ga, $^{67}$Cu, $^{77}$Br, $^{80m}$Br, $^{82}$Rb, $^{86}$Y, $^{89}$Zr, $^{90}$Y, $^{95}$Ru, $^{97}$Ru, $^{99m}$Tc, $^{103}$Ru, $^{105}$Ru, $^{111}$In, $^{113m}$In, $^{113}$Sn, $^{121m}$Te, $^{125m}$Te, $^{125m}$Te, $^{123}$I, $^{124}$I, $^{125}$I, $^{126}$I, $^{131}$I, $^{133}$I, $^{165}$Tm, $^{167}$Tm, $^{168}$Tm, $^{177}$Lu, $^{186}$Re, $^{188}$Re, $^{195m}$Hg, $^{211}$At, $^{212}$Bi, $^{213}$Bi, and $^{225}$Ac. When the conjugated antibodies of the instant invention are employed for radio-immunodetection, the radioisotope is preferably a gamma-emitting isotope. When the conjugated antibodies of the instant invention are employed for detection by ImmunoPET (positron emission tomography), the radioisotope is preferably a positron-emitting isotope such as, without limitation, $^{13}$N, $^{18}$F, $^{89}$Zr, $^{82}$Rb. When the conjugated antibodies of the instant invention are employed for radioimmunotherapy (i.e., the treating of a patient with cancer), the radioisotope is preferably selected from the group consisting of $^{90}$Y, $^{131}$I, $^{177}$Lu, and $^{186}$Re, although other radionuclides such as many of those listed above are also suitable.

The term "radiosensitizer", as used herein, is defined as a molecule administered to animals in therapeutically effective amounts to increase the sensitivity of the cells to radiation. Radiosensitizers are known to increase the sensitivity of cancerous cells to the toxic effects of radiation. Radiosensitizers include, without limitation, 2-nitroimidazole compounds, and benzotriazine dioxide compounds, halogenated pyrimidines, metronidazole, misonidazole, desmethylmisonidazole, pimonidazole, etanidazole, nimorazole, mitomycin C, RSU 1069, SR 4233, E09, RB 6145, nicotinamide, 5-bromodeoxyuridine (BUdR), 5-iododeoxyuridine (IUdR), bromodeoxycytidine, fluorodeoxyuridine (FudR), hydroxyurea, cisplatin, and therapeutically effective analogs and derivatives of the same.

As used herein, a "ligand" refers to a biomolecule, such as a protein or polypeptide, which specifically and/or selectively binds another polypeptide or protein. In a particular embodiment, the term "ligand" refers to a biomolecule which binds to a specific receptor protein located on the surface of a cell.

As used herein, the phrase "complementarity determining region" refers to regions within antibodies which complement an antigen's shape, thereby determining the antibody's affinity and specificity for specific antigens. Complementarity determining regions are noncontiguous regions found within the variable region of both heavy and light chain polypeptides. These particular regions have been described by, for example, Kabat et al. (1977) J. Biol. Chem., 252: 6609-6616; Chothia et al. (1987) J. Mol. Biol., 196:901-917; and MacCallum et al. (1996) J. Mol. Biol., 262:732-745.

As used herein, a linker is a chemical moiety comprising a covalent bond or a chain of atoms that covalently attaches two molecules to each other. In a particular embodiment, the linker comprises amino acids, particularly from 1 to about 25, 1 to about 20, 1 to about 15, 1 to about 10, or 1 to about 5 amino acids.

The following example provides illustrative methods of practicing the instant invention, and is not intended to limit the scope of the invention in any way.

EXAMPLE

A single-chain Fv molecule, E3, was developed and used as a framework scFv. The sequence of E3 is provided in FIG. 5. E3 binds to an artificial epitope composed of a peptide, biotin and streptaviden that does not exist in nature. Accordingly, E3 does not interact with normal human antigens. The heavy chain or the light chain CDR3 loop of E3 was replaced with an MIS loop predicted to be involved in the binding of MIS to MISIIR (FIGS. 1 and 10). Sequences of the hybrid molecules are provided in FIGS. 6-8. FIG. 6 provides the nucleotide and amino acid sequences of RAD-1-0001 (E3 3C2AH3) scFV, wherein the MIS loop is in the antibody H3CDR. FIG. 8 provides the nucleotide and amino acid sequences of RAD-1-0003 (E3 1DQH3) scFv, wherein the MIS loop is in the antibody H3CDR but in a different orientation than RAD-1-0001 (E3 3C2AH3) scFV (namely the MIS loop is placed one residue further out on each side of RAD-1-0001 (E3 3C2AH3) scFV). FIG. 7 provides the nucleotide and amino acid sequence of RAD-1-0002 (E3 1AQKL3) scFv, wherein the MIS loop is in the antibody L3 CDR (notably 3 residues closer to the framework than RAD-1-0003 (E3 1DQH3) scFv).

The ability of the new hybrid scFv molecules to block MIS binding to MISIIR was determined using a reporter gene assay in which signaling through MISIIR on the surface of F19 cells triggers luminescence in the cells (FIG. 3). MIS was added to the cells in the presence or absence of the different scFv molecules and the resulting luminescence was measured (FIG. 4). The results in FIG. 4 demonstrate that RAD-1-0002 and RAD-1-0003 significantly block MIS-induced signaling, thereby indicating that they compete with MIS for its binding site. This indicates that hybrid antibodies have been made that have a new specificity for MISIIR and are capable of modifying signaling through this receptor.

Notably, the third hybrid antibody, RAD-1-0001, did not inhibit signaling. Rather RAD-1-0001 initiated signaling on its own, indicating that RAD-1-0001, or a hybrid antibody based on RAD-1-0001 with further modifications, can trigger agonistic signaling through MISIIR leading to the death of cancer cells expressing the target or survival of neurons expressing the target.

While certain of the preferred embodiments of the present invention have been described and specifically exemplified above, it is not intended that the invention be limited to such embodiments. Various modifications may be made thereto without departing from the scope and spirit of the present invention, as set forth in the following claims.

What is claimed is:

1. An isolated antibody which is immunologically specific for Mullerian Inhibiting Substance Type II Receptor (MISIIR), wherein the complementarity determining region 3 (CDR3) of either the light chain or the heavy chain is replaced with a sequence comprising amino acids 533-550 of SEQ ID NO: 5.

2. The antibody of claim 1, selected from the group consisting of a monoclonal antibody, a single chain Fv antibody, a diabody, a tribody, a tetrabody, a single domain antibody, a minibody, an scFv-Fc molecule, a Fab fragment, a Fab' fragment and a F(ab')$_2$ fragment.

3. The antibody of claim 2, which is a single chain Fv antibody.

4. The antibody of claim 1, wherein said antibody is immunologically specific for the extracellular domain of MISIIR.

5. The antibody of claim 1, wherein said antibody has at least 90% identity with SEQ ID NO: 7, 8, or 9.

6. The antibody of claim 1, wherein said antibody is conjugated to at least one radioisotope, purification tag, imaging agent, contrast agent, chemotherapeutic agent, or cytotoxic molecule.

7. The antibody of claim 1, wherein said antibody has at least 90% identity with SEQ ID NO: 7.

8. The antibody of claim 7, wherein said antibody comprises at least one mutation selected from the group consisting of K109R, R118N, A121L, L111M, S113Y, S120V, and V124Y.

9. A composition comprising at least one antibody of claim 1 and at least one pharmaceutically acceptable carrier.

10. The antibody of claim 1 conjugated to an agent which binds a type I receptor.

11. The antibody of claim 10 conjugated to an agent which binds ALK2, ALK3, or ALK6.

12. The antibody of claim 10, wherein the agent which binds a type I receptor is an antibody which binds the type I receptor or is a ligand of the type I receptor.

13. The antibody of claim 11, wherein the agent which binds a type I receptor is an antibody which binds ALK2, ALK3, or ALK6 or is a ligand of ALK2, ALK3, or ALK6.

14. The antibody of claim 1, wherein said antibody comprises SEQ ID NO: 7, 8, or 9.

\* \* \* \* \*

SEQUENCE LISTING

<160> NUMBER OF SEQ ID NOS: 15

<210> SEQ ID NO 1
<211> LENGTH: 777
<212> TYPE: DNA
<213> ORGANISM: Artificial Sequence
<220> FEATURE:
<223> OTHER INFORMATION: E3 scFv

<400> SEQUENCE: 1

```
atggcccagg tacagctgca gcagtcaggt ccaggactgg tgaagccctc gcagaccctc        60
tcactcacct gtgccatctc cggggacagt gtctctagca agagtgctac ttggaactgg       120
atcaggcagt ccccatcgag aggccttgag tggctgggaa ggacatacta caggtccaag       180
tggtataatg attatgcaga gtctgtgaaa agtcgaataa ccatcaagcc agacacaacc       240
aagaaccatt tctccctgca gctgaagtct gtgactcccg aggacacggc tgtgtattac       300
tgtgcaagtg gaaatggata tctggcctac tggggccagg gcaccctggt caccgtctcc       360
tcatcggcct cggggggcga attgggcggc ggcggctccg gaggaggagg atctggtggt       420
ggtggttcga ctagtcaggc tgtgctgact cagccgtcct cagcgtctgg gacccccggg       480
cagagggtca ccatctcttg ttctggaagc agctccaaca tcgggcagg ctatgatgta       540 cactggtacc agcagcttcc aggaacagcc cccaaactcc tcatctatgg taacagcaat       600
cggccctcag gggtccctga ccgattctct ggctccaagt ctggcacctc agcctccctg       660
gccatcactg ggctccaggc tgaggatgag gctgattatt actgccagtc ctatgacagc       720
agcctgagtg cccataatta tgtcttcgga actgggacca aggtcaccct cctaggc         777
```

<210> SEQ ID NO 2
<211> LENGTH: 840
<212> TYPE: DNA
<213> ORGANISM: Artificial Sequence
<220> FEATURE:
<223> OTHER INFORMATION: Synthetic Sequence

<400> SEQUENCE: 2

```
atggcccagg tacagctgca gcagtcaggt ccaggactgg tgaagccctc gcagaccctc        60
tcactcacct gtgccatctc cggggacagt gtctctagca agagtgctac ttggaactgg       120
atcaggcagt ccccatcgag aggccttgag tggctgggaa ggacatacta caggtccaag       180
tggtataatg attatgcaga gtctgtgaaa agtcgaataa ccatcaagcc agacacaacc       240
aagaaccatt tctccctgca gctgaagtct gtgactcccg aggacacggc tgtgtattac       300
tgtaccaccg acggcttcat cggcaagctg ctcatcagcc tgtcggagga acgcatcagc       360
```

```
gcgcaccacg tcccctacta ctacatggac gtctggggcc agggcaccct ggtcaccgtc      420
tcctcatcgg cctcgggggc cgaattgggc ggcggcggct ccggaggagg aggatctggt      480
ggtggtggtt cgactagtca ggctgtgctg actcagccgt cctcagcgtc tgggaccccc      540
gggcagaggg tcaccatctc ttgttctgga agcagctcca acatcggggc aggctatgat      600
gtacactggt accagcagct tccaggaaca gcccccaaac tcctcatcta tggtaacagc      660
aatcggccct caggggtccc tgaccgattc tctggctcca agtctggcac ctcagcctcc      720
ctggccatca ctgggctcca ggctgaggat gaggctgatt attactgcca gtcctatgac      780
agcagcctga gtgcccataa ttatgtcttc ggaactggga ccaaggtcac cctcctaggc      840
```

```
<210> SEQ ID NO 3
<211> LENGTH: 801
<212> TYPE: DNA
<213> ORGANISM: Artificial Sequence
<220> FEATURE:
<223> OTHER INFORMATION: Synthetic Sequence

<400> SEQUENCE: 3
atggcccagg tacagctgca gcagtcaggt ccaggactgg tgaagccctc gcagaccctc       60
tcactcacct gtgccatctc cggggacagt gtctctagca agagtgctac ttggaactgg      120
atcaggcagt ccccatcgag aggccttgag tggctgggaa ggacatacta caggtccaag      180
tggtataatg attatgcaga gtctgtgaaa agtcgaataa ccatcaagcc agacacaacc      240
aagaaccatt tctccctgca gctgaagtct gtgactcccg aggacacggc tgtgtattac      300
tgtgcaagtg gaaatggata tctggcctac tggggccagg gcaccctggt caccgtctcc      360
tcatcggcct cgggggccga attgggcggc ggcggctccg gaggaggagg atctggtggt      420
ggtggttcga ctagtcaggc tgtgctgact cagccgtcct cagcgtctgg acccccggg      480 cagagggtca ccatctcttg ttctggaagc agctccaaca tcggggcagg ctatgatgta      540
cactggtacc agcagcttcc aggaacagcc cccaaactcc tcatctatgg taacagcaat      600
cggccctcag gggtccctga ccgattctct ggctccaagt ctggcacctc agcctccctg      660
gccatcactg ggctccaggc tgaggatgag gctgattatt actgccagtc cggcaagctg      720
ctcatcagcc tgtcggagga acgcatcagc gcgcaccacg tcccccgctt cggaactggg      780
accaaggtca ccctcctagg c                                                801
```

```
<210> SEQ ID NO 4
<211> LENGTH: 828
<212> TYPE: DNA
<213> ORGANISM: Artificial Sequence
<220> FEATURE:
<223> OTHER INFORMATION: Synthetic Sequence

<400> SEQUENCE: 4
atggcccagg tacagctgca gcagtcaggt ccaggactgg tgaagccctc gcagaccctc       60
tcactcacct gtgccatctc cggggacagt gtctctagca agagtgctac ttggaactgg      120
atcaggcagt ccccatcgag aggccttgag tggctgggaa ggacatacta caggtccaag      180
tggtataatg attatgcaga gtctgtgaaa agtcgaataa ccatcaagcc agacacaacc      240
aagaaccatt tctccctgca gctgaagtct gtgactcccg aggacacggc tgtgtattac      300
tgtgcgagcc ccccggcgg caagctgctc atcagcctgt cggaggaacg catcagcgcg      360
caccacgtcc ccatggacta ctggggccag ggcaccctgg tcaccgtctc ctcatcggcc      420
tcgggggccg aattgggcgg cggcggctcc ggaggaggag gatctggtgg tggtggttcg      480
```

```
actagtcagg ctgtgctgac tcagccgtcc tcagcgtctg ggaccccgg gcagagggtc         540 accatctctt gttctggaag cagctccaac atcgggcag gctatgatgt acactggtac         600
cagcagcttc caggaacagc ccccaaactc ctcatctatg gtaacagcaa tcggccctca       660
ggggtccctg accgattctc tggctccaag tctggcacct cagcctccct ggccatcact        720
gggctccagg ctgaggatga ggctgattat tactgccagt cctatgacag cagcctgagt        780
gcccataatt atgtcttcgg aactgggacc aaggtcaccc tcctaggc                     828
```

<210> SEQ ID NO 5
<211> LENGTH: 560
<212> TYPE: PRT
<213> ORGANISM: Homo sapiens

<400> SEQUENCE: 5

```
Met Arg Asp Leu Pro Leu Thr Ser Leu Ala Leu Val Leu Ser Ala Leu
 1               5                  10                  15

Gly Ala Leu Leu Gly Thr Glu Ala Leu Arg Ala Glu Glu Pro Ala Val
            20                  25                  30

Gly Thr Ser Gly Leu Ile Phe Arg Glu Asp Leu Asp Trp Pro Pro Gly
        35                  40                  45

Ser Pro Gln Glu Pro Leu Cys Leu Val Ala Leu Gly Gly Asp Ser Asn
    50                  55                  60

Gly Ser Ser Ser Pro Leu Arg Val Val Gly Ala Leu Ser Ala Tyr Glu
65                  70                  75                  80

Gln Ala Phe Leu Gly Ala Val Gln Arg Ala Arg Trp Gly Pro Arg Asp
                85                  90                  95

Leu Ala Thr Phe Gly Val Cys Asn Thr Gly Asp Arg Gln Ala Ala Leu
            100                 105                 110

Pro Ser Leu Arg Arg Leu Gly Ala Trp Leu Arg Asp Pro Gly Gly Gln
        115                 120                 125

Arg Leu Val Val Leu His Leu Glu Glu Val Thr Trp Glu Pro Thr Pro
    130                 135                 140

Ser Leu Arg Phe Gln Glu Pro Pro Gly Gly Ala Gly Pro Pro Glu
145                 150                 155                 160

Leu Ala Leu Leu Val Leu Tyr Pro Gly Pro Gly Pro Glu Val Thr Val
                165                 170                 175

Thr Arg Ala Gly Leu Pro Gly Ala Gln Ser Leu Cys Pro Ser Arg Asp
            180                 185                 190

Thr Arg Tyr Leu Val Leu Ala Val Asp Arg Pro Ala Gly Ala Trp Arg
        195                 200                 205

Gly Ser Gly Leu Ala Leu Thr Leu Gln Pro Arg Gly Glu Asp Ser Arg
    210                 215                 220

Leu Ser Thr Ala Arg Leu Gln Ala Leu Leu Phe Gly Asp Asp His Arg
225                 230                 235                 240

Cys Phe Thr Arg Met Thr Pro Ala Leu Leu Leu Leu Pro Arg Ser Glu
                245                 250                 255

Pro Ala Pro Leu Pro Ala His Gly Gln Leu Asp Thr Val Pro Phe Pro
            260                 265                 270

Pro Pro Arg Pro Ser Ala Glu Leu Glu Glu Ser Pro Pro Ser Ala Asp
        275                 280                 285

Pro Phe Leu Glu Thr Leu Thr Arg Leu Val Arg Ala Leu Arg Val Pro
    290                 295                 300

Pro Ala Arg Ala Ser Ala Pro Arg Leu Ala Leu Asp Pro Asp Ala Leu
```

```
                305                 310                 315                 320
Ala Gly Phe Pro Gln Gly Leu Val Asn Leu Ser Asp Pro Ala Ala Leu
                    325                 330                 335

Glu Arg Leu Leu Asp Gly Glu Pro Leu Leu Leu Leu Arg Pro
                340                 345                 350

Thr Ala Ala Thr Thr Gly Asp Pro Ala Pro Leu His Asp Pro Thr Ser
                    355                 360                 365

Ala Pro Trp Ala Thr Ala Leu Ala Arg Arg Val Ala Ala Glu Leu Gln
            370                 375                 380

Ala Ala Ala Ala Glu Leu Arg Ser Leu Pro Gly Leu Pro Pro Ala Thr
385                 390                 395                 400

Ala Pro Leu Leu Ala Arg Leu Ala Leu Cys Pro Gly Gly Pro Gly
                    405                 410                 415

Gly Leu Gly Asp Pro Leu Arg Ala Leu Leu Leu Lys Ala Leu Gln
                420                 425                 430

Gly Leu Arg Val Glu Trp Arg Gly Arg Asp Pro Arg Gly Pro Gly Arg
                    435                 440                 445

Ala Gln Arg Ser Ala Gly Ala Thr Ala Ala Asp Gly Pro Cys Ala Leu
            450                 455                 460

Arg Glu Leu Ser Val Asp Leu Arg Ala Glu Arg Ser Val Leu Ile Pro
465                 470                 475                 480

Glu Thr Tyr Gln Ala Asn Asn Cys Gln Gly Val Cys Gly Trp Pro Gln
                    485                 490                 495

Ser Asp Arg Asn Pro Arg Tyr Gly Asn His Val Val Leu Leu Leu Lys
                500                 505                 510

Met Gln Ala Arg Gly Ala Ala Leu Ala Arg Pro Pro Cys Cys Val Pro
            515                 520                 525

Thr Ala Tyr Ala Gly Lys Leu Leu Ile Ser Leu Ser Glu Glu Arg Ile
                    530                 535                 540

Ser Ala His His Val Pro Asn Met Val Ala Thr Glu Cys Gly Cys Arg
545                 550                 555                 560

<210> SEQ ID NO 6
<211> LENGTH: 804
<212> TYPE: DNA
<213> ORGANISM: Artificial Sequence
<220> FEATURE:
<223> OTHER INFORMATION: Synthetic Sequence

<400> SEQUENCE: 6
atggcccagg tacagctgca gcagtcaggt ccaggactgg tgaagccctc gcagaccctc      60
tcactcacct gtgccatctc cggggacagt gtctctagca agagtgctac ttggaactgg     120
atcaggcagt cccatcgag aggccttgag tggctgggaa ggacatacta caggtccaag      180
tggtataatg attatgcaga gtctgtgaaa agtcgaataa ccatcaagcc agacacaacc     240
aagaaccatt tctccctgca gctgaagtct gtgactcccg aggacacggc tgtgtattac     300
tgtgcaagtg gaaatggata tctggcctac tggggccagg gcaccctggt caccgtctcc     360
tcatcggcct cggggccga attgggcggc ggcggctccg gaggaggagg atctggtggt     420
ggtggttcga ctagtcaggc tgtgctgact cagccgtcct cagcgtctgg gacccccggg     480
cagagggtca ccatctcttg ttctggaagc agctccaaca tcgggcagg ctatgatgta      540 cactggtacc agcagcttcc aggaacagcc cccaaactcc tcatctatgg taacagcaat     600
cggccctcag gggtccctga ccgattctct ggctccaagt ctggcacctc agcctccctg     660
```

```
gccatcactg ggctccaggc tgaggatgag gctgattatt actgccagtc ctatgacagc    720
agcctgagtg cccataatta tgtcttcgga actgggacca aggtcaccct cctaggctcg    780
agccatcacc atcatcacca ttaa                                           804
```

```
<210> SEQ ID NO 7
<211> LENGTH: 280
<212> TYPE: PRT
<213> ORGANISM: Artificial Sequence
<220> FEATURE:
<223> OTHER INFORMATION: Synthetic Sequence

<400> SEQUENCE: 7

Met Ala Gln Val Gln Leu Gln Gln Ser Gly Pro Gly Leu Val Lys Pro
 1               5                  10                  15

Ser Gln Thr Leu Ser Leu Thr Cys Ala Ile Ser Gly Asp Ser Val Ser
            20                  25                  30

Ser Lys Ser Ala Thr Trp Asn Trp Ile Arg Gln Ser Pro Ser Arg Gly
        35                  40                  45

Leu Glu Trp Leu Gly Arg Thr Tyr Tyr Arg Ser Lys Trp Tyr Asn Asp
    50                  55                  60

Tyr Ala Glu Ser Val Lys Ser Arg Ile Thr Ile Lys Pro Asp Thr Thr
65                  70                  75                  80

Lys Asn His Phe Ser Leu Gln Leu Lys Ser Val Thr Pro Glu Asp Thr
                85                  90                  95

Ala Val Tyr Tyr Cys Thr Thr Asp Gly Phe Ile Gly Lys Leu Leu Ile
            100                 105                 110

Ser Leu Ser Glu Glu Arg Ile Ser Ala His His Val Pro Tyr Tyr Tyr
        115                 120                 125

Met Asp Val Trp Gly Gln Gly Thr Leu Val Thr Val Ser Ser Ser Ala
    130                 135                 140

Ser Gly Ala Glu Leu Gly Gly Gly Ser Gly Gly Gly Ser Gly
145                 150                 155                 160

Gly Gly Gly Ser Thr Ser Gln Ala Val Leu Thr Gln Pro Ser Ser Ala
                165                 170                 175

Ser Gly Thr Pro Gly Gln Arg Val Thr Ile Ser Cys Ser Gly Ser Ser
            180                 185                 190

Ser Asn Ile Gly Ala Gly Tyr Asp Val His Trp Tyr Gln Gln Leu Pro
        195                 200                 205

Gly Thr Ala Pro Lys Leu Leu Ile Tyr Gly Asn Ser Asn Arg Pro Ser
    210                 215                 220

Gly Val Pro Asp Arg Phe Ser Gly Ser Lys Ser Gly Thr Ser Ala Ser
225                 230                 235                 240

Leu Ala Ile Thr Gly Leu Gln Ala Glu Asp Glu Ala Asp Tyr Tyr Cys
                245                 250                 255

Gln Ser Tyr Asp Ser Ser Leu Ser Ala His Asn Tyr Val Phe Gly Thr
            260                 265                 270

Gly Thr Lys Val Thr Leu Leu Gly
        275                 280

<210> SEQ ID NO 8
<211> LENGTH: 267
<212> TYPE: PRT
<213> ORGANISM: Artificial Sequence
<220> FEATURE:
<223> OTHER INFORMATION: Synthetic Sequence

<400> SEQUENCE: 8
```

Met Ala Gln Val Gln Leu Gln Gln Ser Gly Pro Gly Leu Val Lys Pro
1               5                   10                  15

Ser Gln Thr Leu Ser Leu Thr Cys Ala Ile Ser Gly Asp Ser Val Ser
            20                  25                  30

Ser Lys Ser Ala Thr Trp Asn Trp Ile Arg Gln Ser Pro Ser Arg Gly
        35                  40                  45

Leu Glu Trp Leu Gly Arg Thr Tyr Tyr Arg Ser Lys Trp Tyr Asn Asp
    50                  55                  60

Tyr Ala Glu Ser Val Lys Ser Arg Ile Thr Ile Lys Pro Asp Thr Thr
65                  70                  75                  80

Lys Asn His Phe Ser Leu Gln Leu Lys Ser Val Thr Pro Glu Asp Thr
                85                  90                  95

Ala Val Tyr Tyr Cys Ala Ser Gly Asn Gly Tyr Leu Ala Tyr Trp Gly
            100                 105                 110

Gln Gly Thr Leu Val Thr Val Ser Ser Ala Ser Gly Ala Glu Leu
        115                 120                 125

Gly Gly Gly Gly Ser Gly Gly Gly Ser Gly Gly Gly Ser Thr
    130                 135                 140

Ser Gln Ala Val Leu Thr Gln Pro Ser Ser Ala Ser Gly Thr Pro Gly
145                 150                 155                 160

Gln Arg Val Thr Ile Ser Cys Ser Gly Ser Ser Ser Asn Ile Gly Ala
                165                 170                 175

Gly Tyr Asp Val His Trp Tyr Gln Gln Leu Pro Gly Thr Ala Pro Lys
            180                 185                 190

Leu Leu Ile Tyr Gly Asn Ser Asn Arg Pro Ser Gly Val Pro Asp Arg
        195                 200                 205

Phe Ser Gly Ser Lys Ser Gly Thr Ser Ala Ser Leu Ala Ile Thr Gly
    210                 215                 220

Leu Gln Ala Glu Asp Glu Ala Asp Tyr Tyr Cys Gln Ser Gly Lys Leu
225                 230                 235                 240

Leu Ile Ser Leu Ser Glu Glu Arg Ile Ser Ala His His Val Pro Arg
                245                 250                 255

Phe Gly Thr Gly Thr Lys Val Thr Leu Leu Gly
            260                 265

<210> SEQ ID NO 9
<211> LENGTH: 276
<212> TYPE: PRT
<213> ORGANISM: Artificial Sequence
<220> FEATURE:
<223> OTHER INFORMATION: Synthetic Sequence

<400> SEQUENCE: 9

Met Ala Gln Val Gln Leu Gln Gln Ser Gly Pro Gly Leu Val Lys Pro
1               5                   10                  15

Ser Gln Thr Leu Ser Leu Thr Cys Ala Ile Ser Gly Asp Ser Val Ser
            20                  25                  30

Ser Lys Ser Ala Thr Trp Asn Trp Ile Arg Gln Ser Pro Ser Arg Gly
        35                  40                  45

Leu Glu Trp Leu Gly Arg Thr Tyr Tyr Arg Ser Lys Trp Tyr Asn Asp
    50                  55                  60

Tyr Ala Glu Ser Val Lys Ser Arg Ile Thr Ile Lys Pro Asp Thr Thr
65                  70                  75                  80

Lys Asn His Phe Ser Leu Gln Leu Lys Ser Val Thr Pro Glu Asp Thr
                85                  90                  95

```
Ala Val Tyr Tyr Cys Ala Ser Pro Gly Gly Lys Leu Leu Ile Ser
            100             105             110

Leu Ser Glu Glu Arg Ile Ser Ala His His Val Pro Met Asp Tyr Trp
        115             120             125

Gly Gln Gly Thr Leu Val Thr Val Ser Ser Ala Ser Gly Ala Glu
    130             135             140

Leu Gly Gly Gly Ser Gly Gly Gly Ser Gly Gly Gly Ser
145             150             155             160

Thr Ser Gln Ala Val Leu Thr Gln Pro Ser Ala Ser Gly Thr Pro
                165             170             175

Gly Gln Arg Val Thr Ile Ser Cys Ser Gly Ser Ser Asn Ile Gly
        180             185             190

Ala Gly Tyr Asp Val His Trp Tyr Gln Gln Leu Pro Gly Thr Ala Pro
        195             200             205

Lys Leu Leu Ile Tyr Gly Asn Ser Asn Arg Pro Ser Gly Val Pro Asp
    210             215             220

Arg Phe Ser Gly Ser Lys Ser Gly Thr Ser Ala Ser Leu Ala Ile Thr
225             230             235             240

Gly Leu Gln Ala Glu Asp Glu Ala Asp Tyr Tyr Cys Gln Ser Tyr Asp
                245             250             255

Ser Ser Leu Ser Ala His Asn Tyr Val Phe Gly Thr Gly Thr Lys Val
            260             265             270

Thr Leu Leu Gly
        275

<210> SEQ ID NO 10
<211> LENGTH: 121
<212> TYPE: PRT
<213> ORGANISM: Artificial Sequence
<220> FEATURE:
<223> OTHER INFORMATION: E3 heavy chain

<400> SEQUENCE: 10

Met Ala Gln Val Gln Leu Gln Gln Ser Gly Pro Gly Leu Val Lys Pro
1               5                   10                  15

Ser Gln Thr Leu Ser Leu Thr Cys Ala Ile Ser Gly Asp Ser Val Ser
            20                  25                  30

Ser Lys Ser Ala Thr Trp Asn Trp Ile Arg Gln Ser Pro Ser Arg Gly
        35                  40                  45

Leu Glu Trp Leu Gly Arg Thr Tyr Tyr Arg Ser Lys Trp Tyr Asn Asp
    50                  55                  60

Tyr Ala Glu Ser Val Lys Ser Arg Ile Thr Ile Lys Pro Asp Thr Thr
65                  70                  75                  80

Lys Asn His Phe Ser Leu Gln Leu Lys Ser Val Thr Pro Glu Asp Thr
                85                  90                  95

Ala Val Tyr Tyr Cys Ala Ser Gly Asn Gly Tyr Leu Ala Tyr Trp Gly
            100                 105                 110

Gln Gly Thr Leu Val Thr Val Ser Ser
        115                 120

<210> SEQ ID NO 11
<211> LENGTH: 131
<212> TYPE: PRT
<213> ORGANISM: Artificial Sequence
<220> FEATURE:
<223> OTHER INFORMATION: 3C2A heavy chain
```

<400> SEQUENCE: 11

```
Glu Val Gln Leu Val Glu Ser Gly Gly Gly Leu Val Lys Pro Gly Gly
1               5                   10                  15

Ser Leu Arg Leu Thr Cys Val Ala Ser Gly Phe Thr Phe Ser Asp Val
            20                  25                  30

Trp Leu Asn Trp Val Arg Gln Ala Pro Gly Lys Gly Leu Glu Trp Val
        35                  40                  45

Gly Arg Ile Lys Ser Arg Thr Asp Gly Gly Thr Thr Asp Tyr Ala Ala
50                  55                  60

Ser Val Lys Gly Arg Phe Thr Ile Ser Arg Asp Asp Ser Lys Asn Thr
65                  70                  75                  80

Leu Tyr Leu Gln Met Asn Ser Leu Lys Thr Glu Asp Thr Ala Val Tyr
                85                  90                  95

Ser Cys Thr Thr Asp Gly Phe Ile Met Ile Arg Gly Val Ser Glu Asp
            100                 105                 110

Tyr Tyr Tyr Tyr Tyr Met Asp Val Trp Gly Lys Gly Thr Thr Val Thr
            115                 120                 125

Val Ser Ser
    130
```

<210> SEQ ID NO 12
<211> LENGTH: 18
<212> TYPE: PRT
<213> ORGANISM: Artificial Sequence
<220> FEATURE:
<223> OTHER INFORMATION: Synthetic Sequence

<400> SEQUENCE: 12

```
Gly Lys Leu Leu Ile Ser Leu Ser Glu Glu Arg Ile Ser Ala His His
1               5                   10                  15

Val Pro
```

<210> SEQ ID NO 13
<211> LENGTH: 10
<212> TYPE: PRT
<213> ORGANISM: Artificial Sequence
<220> FEATURE:
<223> OTHER INFORMATION: Synthetic Sequence

<400> SEQUENCE: 13

```
Met Ile Arg Gly Val Ser Glu Asp Tyr Tyr
1               5                   10
```

<210> SEQ ID NO 14
<211> LENGTH: 139
<212> TYPE: PRT
<213> ORGANISM: Artificial Sequence
<220> FEATURE:
<223> OTHER INFORMATION: Synthetic Sequence

<400> SEQUENCE: 14

```
Glu Val Gln Leu Val Glu Ser Gly Gly Gly Leu Val Lys Pro Gly Gly
1               5                   10                  15

Ser Leu Arg Leu Thr Cys Val Ala Ser Gly Phe Thr Phe Ser Asp Val
            20                  25                  30

Trp Leu Asn Trp Val Arg Gln Ala Pro Gly Lys Gly Leu Glu Trp Val
        35                  40                  45

Gly Arg Ile Lys Ser Arg Thr Asp Gly Gly Thr Thr Asp Tyr Ala Ala
50                  55                  60
```

```
Ser Val Lys Gly Arg Phe Thr Ile Ser Arg Asp Asp Ser Lys Asn Thr
 65                  70                  75                  80

Leu Tyr Leu Gln Met Asn Ser Leu Lys Thr Glu Asp Thr Ala Val Tyr
                 85                  90                  95

Ser Cys Thr Thr Asp Gly Phe Ile Gly Lys Leu Leu Ile Ser Leu Ser
                100                 105                 110

Glu Glu Arg Ile Ser Ala His His Val Pro Tyr Tyr Tyr Met Asp Val
            115                 120                 125

Trp Gly Lys Gly Thr Thr Val Thr Val Ser Ser
            130                 135

<210> SEQ ID NO 15
<211> LENGTH: 142
<212> TYPE: PRT
<213> ORGANISM: Artificial Sequence
<220> FEATURE:
<223> OTHER INFORMATION: Synthetic Sequence

<400> SEQUENCE: 15

Met Ala Gln Val Gln Leu Gln Gln Ser Gly Pro Gly Leu Val Lys Pro
  1               5                  10                  15

Ser Gln Thr Leu Ser Leu Thr Cys Ala Ile Ser Gly Asp Ser Val Ser
                 20                  25                  30

Ser Lys Ser Ala Thr Trp Asn Trp Ile Arg Gln Ser Pro Ser Arg Gly
             35                  40                  45

Leu Glu Trp Leu Gly Arg Thr Tyr Tyr Arg Ser Lys Trp Tyr Asn Asp
 50                  55                  60

Tyr Ala Glu Ser Val Lys Ser Arg Ile Thr Ile Lys Pro Asp Thr Thr
 65                  70                  75                  80

Lys Asn His Phe Ser Leu Gln Leu Lys Ser Val Thr Pro Glu Asp Thr
                 85                  90                  95

Ala Val Tyr Tyr Cys Thr Thr Asp Gly Phe Ile Gly Lys Leu Leu Ile
                100                 105                 110

Ser Leu Ser Glu Glu Arg Ile Ser Ala His His Val Pro Tyr Tyr Tyr
            115                 120                 125

Met Asp Val Trp Gly Gln Gly Thr Leu Val Thr Val Ser Ser
            130                 135                 140
```